United States Patent [19]

Mori

[11] Patent Number: 4,978,186

[45] Date of Patent: Dec. 18, 1990

[54] LIGHT RADIATION DEVICE FOR USE IN MEDICAL TREATMENT

[76] Inventor: Kei Mori, 3-16-3-501, Kaminoge, Setagaya-Ku, Tokyo, Japan

[21] Appl. No.: 380,954

[22] Filed: Jul. 17, 1989

[30] Foreign Application Priority Data

Sep. 26, 1988 [JP] Japan .............................. 63-239953

[51] Int. Cl.$^5$ .......................... G02B 6/00; F21V 7/04; A61M 5/00
[52] U.S. Cl. .............................. 350/96.10; 350/96.22; 350/96.23; 350/96.24; 362/32; 606/9; 606/16; 128/397; 128/395
[58] Field of Search ............... 350/96.10, 96.15, 96.20, 350/96.22, 96.23, 96.24; 362/32; 606/9, 11, 15, 16; 128/362, 395, 396, 397

[56] References Cited

U.S. PATENT DOCUMENTS

| 4,107,763 | 8/1978 | Thiel et al. | 362/32 |
| 4,723,825 | 2/1988 | Herold | 350/96.10 |
| 4,771,371 | 9/1988 | Mori | 362/32 X |
| 4,785,811 | 11/1988 | Mori | 362/32 X |
| 4,796,967 | 1/1989 | Mori | 350/96.10 |
| 4,844,579 | 7/1989 | Mori | 350/96.10 |
| 4,898,439 | 2/1990 | Mori | 350/96.10 |
| 4,911,511 | 3/1990 | Mori | 350/96.10 |

FOREIGN PATENT DOCUMENTS

| 0208309 | 1/1987 | European Pat. Off. | 350/96.10 X |
| 2184021 | 6/1987 | United Kingdom | 350/96.10 X |

*Primary Examiner*—Brian Healy
*Attorney, Agent, or Firm*—Jordan and Hamburg

[57] ABSTRACT

A light radiation device for use in medical treatment is disclosed. The device comprises a fiber optic cable, a light radiator and a holding pipe. The fiber optic cable transmits therethrough visible light rays and radiates the same from its end surface. The light radiator has a number of densely bundled tapered columns placed opposite the end surface of the fiber optic cable, each column consisting of a plurality of optical conductors. The holding pipe holds the light-radiating end of the fiber optic cable at one end and a light-receiving end of the light radiator at the other end so as to allow the light to pass therethrough and enter into the light radiator.

13 Claims, 4 Drawing Sheets

LIGHT RADIATION DEVICE FOR USE IN MEDICAL TREATMENT

BACKGROUND OF THE INVENTION

The present invention relates to a light radiation device for use in medical treatment and more particularly to a light radiation device capable of irradiating a patient's scalp with light rays transmitted through a fiber optic cable.

In recent years, a large number of persons suffer from in curable diseases such as gout, neuralgia and rheumatism, or from pain caused by injury scars, bone fracture scars or from ill-defined diseases. Furthermore, no one can be free from aging skin which progresses gradually from a comparatively young age. On the other hand, the present applicant has previously proposed focusing the sun's rays or artificial light rays, by using lenses or the like, to guide the focused light rays into a fiber optic cable and to transmit them to any place where the light is needed for illumination or for other purposes such as cultivating plants, chlorella, fish and the like. Through research it has been found that visible light not containing ultraviolet and infrared rays is effective not only for promoting health and for preventing people's skin from aging by increasing a living body activity but also by noticeably helping to heal gout, neuralgia, bedsores, rheumatism, burn scars, skin diseases, bone fracture scars etc. and in relieving pain from such diseases.

Furthermore, on the basis of the above-mentioned inventor's discovery, the applicant has previously proposed a light radiating device for radiating the visible light containing none of the harmful ultraviolet rays and infrared rays with the aim of using it for healing various kinds of diseases, for giving beauty treatments and for promoting health.

The present applicant has proposed a light radiation device for use in medical treatment comprised of a fiber optic cable for receiving sunlight or artificial light at its input end, and for transmitting the light therethrough, a hood member installed at the light-emitting end portion of said fiber optic cable and a chair for the patient. The light to be transmitted through said fiber optic cable is one that corresponds to the visible-spectrum light obtainable in the various ways previously proposed by the present applicant.

At the time of medical treatment, a patient is placed in the chair and the visible-spectrum of light thus transmitted through the fiber optic cable is radiated onto the diseased part of the patient.

As mentioned above, the light to be radiated onto the diseased part of the patient is the one that corresponds to the visible-spectrum components of the sunlight and is free from the harmful elements such as ultraviolet and infrared rays. Consequently, it may be possible to make medical treatments safe with no fear of exposing a patient to harmful ultraviolet and infrared rays. However, the above-mentioned light radiation device, which is mainly used for healing the above-mentioned various kinds of diseases by radiating the light onto the skin's surface has proved inadequate in the case of healing a patient's scalp since said light may be obstructed by hair and thereby cannot reach the surface of the skin.

SUMMARY OF THE INVENTION

It is an object of the present invention to provide a light radiation device which is suitable for irradiating the scalp of a patient with the light transmitted through a fiber optic cable.

It is another object of the present invention to provide a light radiation device for use in medical treatment which has a number of densely bundled optical conductors, each having a tapered tip for emitting light rays and thereby able to effectively and directly radiate the light rays onto the patient's scalp without being obstructed by hair.

DESCRIPTION OF THE PREFERRED EMBODIMENTS

Figure 1:
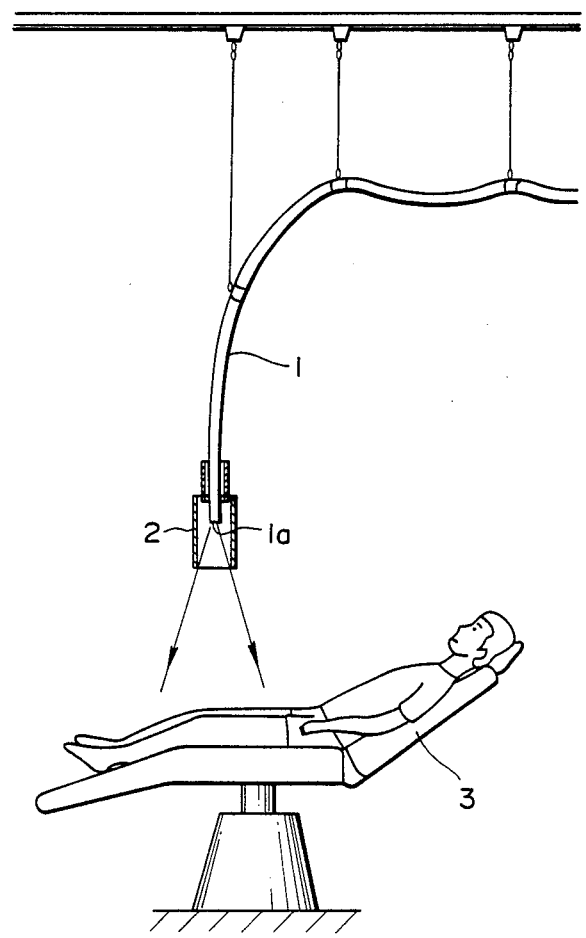
FIG. 1 is a view for explaining an embodiment of a light radiation device previously proposed by the present applicant for use in medical treatment.

FIG. 1 is a construction view for explaining an embodiment of a light radiation device for use in medical treatment as previously proposed by the present applicant. In FIG. 1, numeral 1 designates a fiber optic cable for receiving sunlight or artificial light at its input end, not shown in FIG. 1, and for transmitting the same therethrough. The light to be transmitted through said fiber optic cable 1 is one that corresponds to the visible-spectrum of light (i.e. white-colored light) obtainable in various ways as previously proposed by the present applicant. In FIG. 1, numeral 2 designates a hood member installed at the light-emitting end portion 1a of said fiber optic cable and numeral 3 designates a chair for a patient. At the time of medical treatment, a patient is placed in the chair 3 and the visible-spectrum of light thus transmitted through the fiber optic cable 1 is radiated onto the diseased part of the patient.

As mentioned above, the light to be radiated onto the diseased part of the patient is the one that corresponds to the visible-spectrum components of the sunlight and is free from the harmful elements such as ultraviolet and infrared rays. Consequently, it may be possible to make medical treatments safe with no fear of exposing a patient to harmful ultraviolet and infrared rays. However, the above-mentioned light radiation device, which is mainly used for healing the above-mentioned various kinds of diseases by radiating the light onto the skin's surface has proved inadequate in the case of healing a patient's scalp since said light may be obstructed by hair and thereby cannot reach the surface of the skin.

Figure 2:
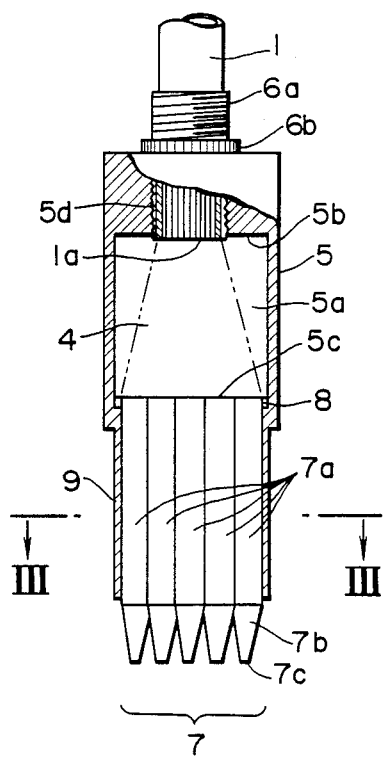
FIG. 2 is a perspective view for explaining an embodiment of the light radiation device for use in medical treatment according to the present invention.
Figure 3:
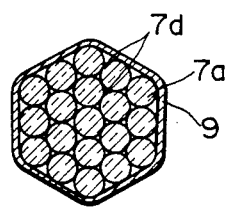
FIG. 3 is a cross section taken on line III—III of FIG. 2.

FIG. 2 is a basic sectional view for explaining an embodiment of a light radiation device for use in medical treatment according to the present invention. In FIG. 2, 1 is a fiber optic cable for transmitting therethrough sunlight i.e. visible light not containing ultraviolet and infrared rays 4 collected by a solar ray collecting device not shown in FIG. 2 and emitting the same from its end's surface 1a. Numeral 5 is a holding pipe having an upper through-hole with thread 5d for coaxially fixing therein a light-emitting end of the fiber optic cable 1. At this time said fiber optic cable 1 is secured to the holding pipe 5 by the use of a nut 6b engaging with a threaded fitting 6a fixed onto the cable's end in such a way that the cable's end surface may be substantially flush with an upper inner surface 5a of the holding pipe 5. A lower end-surface 5c of the holding pipe 5 is open to set therein an upper end of the light radiator 7 opposite the light emitting end 1a of the fiber optic cable 1. At this time said upper end of the light radiator 7 is locked by adhering its circumference to the inner wall of the holding pipe with an adhesive 8. The light radiator 7 is a compact bundle of a plurality of round columns 7a, each having a tapered end. As shown in FIG. 3 which is a cross section taken on line III—III of FIG. 2, said bundle of columns 7a is covered with a thermally shrinkable tube 9 of a hexagonal cross section and receives visible light 4 and emits the same from its light emitting end 7c. The round column 7a is composed of glass, transparent resin such as an acrylic resin, a core and a light conductor having a clad layer. When the light-emitting end (tapered teeth) 7c of the light radiation device is placed on the patient's head, the visible light delivered through the fiber optic cable 1 can be directly radiated onto the patient's scalp without being obstructed by hair. Although the light radiation device shown in FIG. 2 is formed with light-emitting teeth 7C aligned on the same plane, it is also possible to arrange the light-emitting teeth 7c to form a concave surface matching a person's head so as to more effectively irradiate the patient's scalp.

Figure 4:
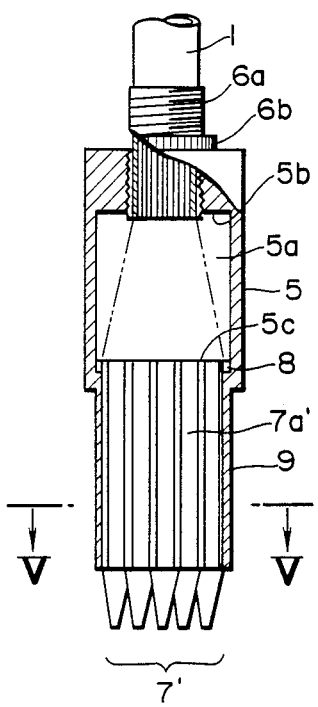
FIG. 4 is a view for explaining an embodiment of the light radiation device when in use.
Figure 5:
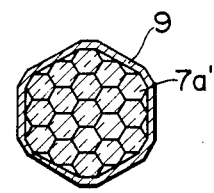
FIG. 5 is a cross section taken on line V—V of FIG. 4.

FIG. 4 is a view for explaining another embodiment of the light radiation device which is characterized by adopting hexagonal radiators 7' each consisting of hexagonal columns 7a', while in the previously described embodiment each hexagonal radiator 7, constructed of round columns 7a, partially in contact with each other with a large number of gaps 7d formed there-between resulting in the decreased radiation efficiency of the device. Referring to FIG. 4, since other components of the device are identical to the previously described embodiment of FIG. 2, the same parts are given with the same references and explanations are omitted. As shown in FIG. 5, each hexagonal radiator 7' is composed of a number of hexagonal columns 7a', which are in close contact with each other and side-by-side so as not to form gaps in between. Such a construction of the radiator 7' improves the light radiation efficiency of the device. The radiator 7' can be easily formed by uniformly compressing the circumference of the round columns 7a as shown in FIG. 2.

Figure 6:
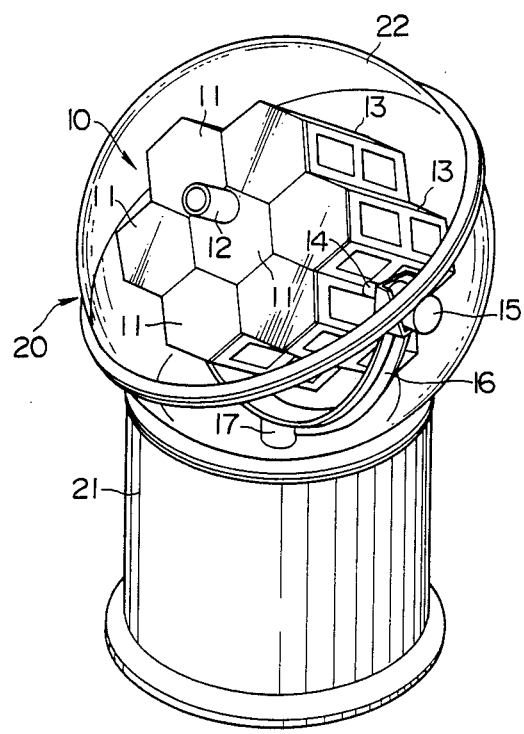
FIG. 6 is a view for explaining an embodiment of a solar ray collecting device to be used with the present invention.

FIG. 6 is an entire perspective view illustrating, by way of example, a solar ray collecting device for guiding the sunlight into the afore-mentioned fiber optic cable 1. In FIG. 6, a capsule 20 for use in the solar ray collecting device is constructed of a cylindrical body 21 and a transparent domed head 22. As shown in FIG. 6, the solar ray collecting device 10 is accommodated in the capsule when the device is being used. The solar ray collecting device comprises one lens, several lenses or possibly a large number of lenses (for example, 7, 19, 61 or 1600 lenses) 11, a solar position sensor 12 for detecting the sun's location, a support frame body 13 for integrally holding the lens 11 and a sensor 12, a first revolving shaft 14 for rotating the support frame 13, a first motor 15 for rotating the first revolving shaft 14, a support arm 16 for supporting the lens 11 or the motor 15, a second revolving shaft 17 installed so as to intersect the first revolving shaft 14 perpendicularly thereto, and a second motor, not shown in FIG. 3, for rotating the second revolving shaft 17.

The direction of the sun is detected by means of the solar position sensor 12 and its detection signal controls the first and second motors so as to always direct the lens 11 toward the sun, and the sunlight focused by the lens 11 is guided into the fiber optic cable, not shown in FIG. 6, through its end surface set at the focal point of the lens. The guided sunlight is transmitted through the fiber optic cable to anywhere the light is needed.

Concerning the above-mentioned solar ray collecting device, several types of devices have been proposed by the present applicant. They are devices respectively having a lens or several lenses (2 to 4 lenses) or a large number of lenses (for instance 7, 19, 61 or 1600 lenses) according to the purpose for its use.

Figure 7:
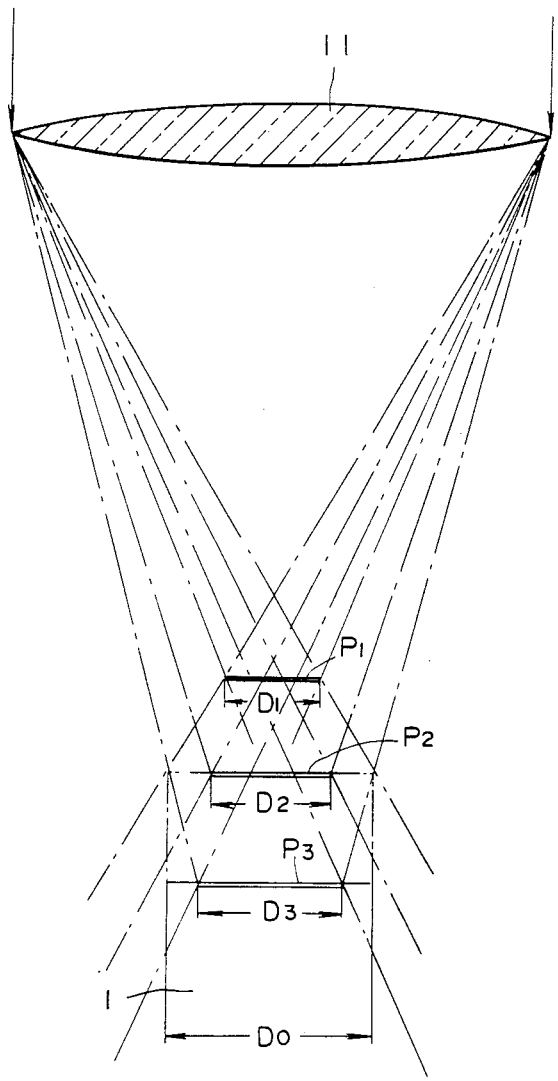
FIG. 7 is a view for explaining an embodiment for guiding the sunlight into a fiber optic cable.

FIG. 7 is a view for explaining how to guide the light rays corresponding to the visible-spectrum components of the sunlight into a fiber optic cable 1. In FIG. 7, 11 is a lens consisting of a Fresnel lens or the like, and the sunlight focused by the lens system 11 is guided into a fiber optic cable 1 as mentioned before. In the case of focusing the sunlight through the lens system, the solar image has a central portion consisting of almost white light and a circumferential portion containing therein a large amount of the light components having wavelengths corresponding to the focal point of the lens system. Namely, in the case of focusing sunlight through the lens system, the focal point and the size of the solar image will vary in accordance with the wavelengths of the light components. For instance, the blue color light, having a short wavelength, makes a solar image of the diameter D1 at the position P1. Furthermore, the green color light makes a solar image of the diameter D2 at the position P2 and the red color light makes a solar image of the diameter D3 at the position P3. Consequently, as shown in FIG. 7, when the light-receiving end-surface of the fiber optic cable 1 is set at the position P1, it is possible to collect sunlight containing plenty of the blue color components at the circumferential portion thereof.

When the light-receiving end-surface of the fiber optic cable 1 is set at the position P2, it is possible to collect the sunlight containing plenty of the green color components at the circumferential portion thereof. When the light-receiving end-surface of the fiber optic cable 1 is set at the position P3 it is possible to collect the sunlight containing plenty of red color components at the circumferential portion thereof. In each case, the diameter of the fiber optic cable can be selected in accordance with the light components to be collected. For instance, the required diameters of the fiber optic cables are D1, D2 and D3 respectively depending on the colors of the light rays to be stressed, i.e. the blue, green or red colors. In such a way, the required amount of the fiber optic cable can be saved and thereby the sunlight containing therein plenty of desired color components can be collected most effectively. And further, as shown in FIG. 7, if the diameter of the light-receiving end-surface of the fiber optic cable is enlarged to D0, it may be possible to collect visible light containing therein all of the wavelengths of the components.

The visible light thus obtained is transmitted through the fiber optic cable 1 to the light radiation device according to the present invention, wherein the light is guided into the tapered end portion 7b, reflected at the circumference thereof and emitted from the light-emitting ends 7c.

As is apparent from the foregoing description, according to the present invention, it may be possible to provide a light radiation device for use in medical treatment which has a number of densely bundled optical conductors, each having a tapered tip for emitting light rays and thereby can effectively and directly radiate the light rays onto the patient's scalp without being obstructed by hair.

I claim:

1. A light radiation device for treating a person's scalp, comprising a fiber optic cable means for transmitting visible light rays, said cable means having a light-emitting end, a light radiator means comprising a housing, said light-emitting end of said cable means being mounted on said housing, optical conductor means mounted on said housing at a position spaced from said light-emitting end, said optical conductor means having a light-receiving end spaced from said light-emitting end of said cable means such that light rays are transmitted from said light-emitting end to said light-receiving end, said optical conductor means comprising a plurality of elongated and parallel light-conductor elements each having a main portion and an end portion, enclosure means joined to said housing and disposed about said main portion of said conductor elements, said enclosure means having an outer end, said end portion of said conductor elements extending outwardly of said enclosure means beyond said outer end, each of said end portions of said conductor element being tapered to thereby define a plurality of tapered teeth, said tapered teeth being placeable on a person's scalp without being obstructed by said person's hair to effect light radiation of said person's scalp.

2. A light radiation device according to claim 1, wherein said enclosure means has a substantially circular cross-sectional configuration.

3. A light radiation device according to claim 1, wherein said enclosure means has a substantially hexagonal cross-sectional configuration.

4. A light radiation device according to claim 1, wherein each of said conductor elements is an elongated element of the same longitudinal length.

5. A light radiation device according to claim 4, wherein each of said end portions of said conductor elements has an outer terminating end dusposed in a common plane.

6. A light radiation device according to claim 5, wherein each of said end portions of each of said conductor elements has a progressively decreasing cross-sectional area as said outer terminating end is approached.

7. A light radiation device according to claim 1, wherein each of said end portions of each of said conductor elements has an outer terminating end disposed such that the plurality of outer terminating ends of said plurality of conductor elements define a concave surface generally matching the convex configuration of a person's head.

8. A light radiation device according to claim 1, wherein each of said conductor elements has a circular cross-sectional configuration.

9. A light radiation device according to claim 1, wherein each of said conductor elements has a substantially hexagonal cross-sectional configuration.

10. A light radiation device according to claim 9, wherein each of said conductor elements has planar side walls with the planar side walls of each conductor element being in abutting contact with the planar side walls of each juxtaposed conductor element.

11. A light radiation device according to claim 1, wherein said enclosure means comprises a thermally shrinkable tube disposed about said main portions of said conductor elements.

12. A light radiation device according to claim 11 further comprising adhesive means adhesively affixing said tube to said housing.

13. A light radiation device according to claim 1, wherein said enclosure means comprises a tube in which said conductor elements are disposed, said housing comprising a pipe, and adhesive means adhesively securing said tube to said pipe.

* * * * *